United States Patent
Hamilton et al.

(10) Patent No.: US 10,071,221 B2
(45) Date of Patent: Sep. 11, 2018

(54) REMOVABLE ANGLED GUIDEWIRE STORAGE DEVICE

(71) Applicant: GYRUS ACMI, INC., Southborough, MA (US)

(72) Inventors: Bruce S. Hamilton, Hampstead, NH (US); Richard P. Stecchi, Salem, NH (US); Antonio E. Prats, Shrewsbury, MA (US); Benjamin T. Mroczek, Boxford, MA (US)

(73) Assignee: GYRUS ACMI, INC., Southborough, MA (US)

( * ) Notice: Subject to any disclaimer, the term of this patent is extended or adjusted under 35 U.S.C. 154(b) by 478 days.

(21) Appl. No.: 14/721,389

(22) Filed: May 26, 2015

(65) Prior Publication Data
US 2015/0352317 A1 Dec. 10, 2015

Related U.S. Application Data (60) Provisional application No. 62/007,958, filed on Jun. 5, 2014.

(51) Int. Cl.
*A61M 25/00* (2006.01)
*A61B 1/00* (2006.01)
(Continued)

(52) U.S. Cl.
CPC ....... *A61M 25/002* (2013.01); *A61B 1/00131* (2013.01); *A61B 50/30* (2016.02);
(Continued)

(58) Field of Classification Search
CPC .......... A61M 25/002; A61M 25/09041; A61M 25/09; A61M 25/0113; A61M 2025/09116; A61B 50/30; A61B 1/00131
(Continued)

(56) References Cited

U.S. PATENT DOCUMENTS

| | | | |
|---|---|---|---|
| 3,633,758 A | 1/1972 | Morse | |
| 6,551,281 B1 * | 4/2003 | Raulerson | A61M 25/09041 604/164.13 |

(Continued)

FOREIGN PATENT DOCUMENTS

| | | |
|---|---|---|
| CN | 101804235 A | 8/2010 |
| EP | 1407793 A1 | 4/2004 |

(Continued)

OTHER PUBLICATIONS

Search Report and Written Opinion for Application No. PCT/US2015/032395, dated Aug. 17, 2015.
(Continued)

*Primary Examiner* — Steven A. Reynolds
(74) *Attorney, Agent, or Firm* — The Dobrusin Law Firm P.C.

(57) ABSTRACT

An article that includes a guidewire and a removable angled guidewire storage device. The guidewire comprises an angled portion that is at an angle relative to a reminder of the guidewire. A distal end of the removable angled guidewire storage device has a conical shape having a wall that is configured to maintain the angled portion of the guidewire at the angle relative to the reminder of the guidewire. A proximal end of the removable angled guidewire storage device has an opening that is adapted to fit over at least a portion of an introducer. The angled guidewire storage device includes an internal channel having walls extending between the conical shape at the distal end of the removable angled guidewire storage device and the opening at the proximal end of the angled guidewire storage device for receiving and holding the guidewire.

16 Claims, 2 Drawing Sheets

(51) Int. Cl.
*A61M 25/01* (2006.01)
*A61B 50/30* (2016.01)
*A61M 25/09* (2006.01)

(52) U.S. Cl.
CPC ........ *A61M 25/0113* (2013.01); *A61M 25/09* (2013.01); *A61M 25/09041* (2013.01); *A61M 2025/09075* (2013.01); *A61M 2025/09116* (2013.01); *A61M 2025/09141* (2013.01); *A61M 2205/0216* (2013.01)

(58) Field of Classification Search
USPC .................................. 206/363, 370; 604/263
See application file for complete search history.

(56) References Cited

U.S. PATENT DOCUMENTS

| | | | |
|---|---|---|---|
| 2003/0171771 A1* | 9/2003 | Anderson | A61B 17/12172 606/200 |
| 2004/0147880 A1 | 7/2004 | Duffy et al. | |
| 2005/0054953 A1 | 3/2005 | Ryan et al. | |
| 2005/0061698 A1 | 3/2005 | Delaney et al. | |
| 2006/0253048 A1 | 11/2006 | Jones et al. | |
| 2007/0185413 A1 | 8/2007 | Asai et al. | |
| 2009/0182281 A1 | 7/2009 | Kurth et al. | |
| 2011/0178506 A1* | 7/2011 | Numata | A61M 25/002 604/528 |
| 2012/0239066 A1 | 9/2012 | Levine et al. | |
| 2012/0283667 A1* | 11/2012 | Deeds | A61M 25/002 604/265 |

FOREIGN PATENT DOCUMENTS

| | | |
|---|---|---|
| EP | 1570878 A2 | 9/2005 |
| JP | 06-013847 U | 2/1994 |
| JP | 2004290395 A | 10/2004 |
| JP | 2004-337361 A | 12/2004 |
| JP | 2008049017 A | 3/2008 |
| WO | 2005/087304 A1 | 1/2008 |
| WO | 2010/035581 A | 2/2012 |
| WO | 2014/010335 A1 | 1/2014 |

OTHER PUBLICATIONS

Japanese Office Action for Japanese Patent Application No. 2016-571349 dated Nov. 14, 2017.
Japanese Office Action for Japanese Patent Application No. 2016-571349, dated May 8, 2018.
European Office Acton for European Application No. 15730573.1, dated May 28, 2018.

* cited by examiner

REMOVABLE ANGLED GUIDEWIRE STORAGE DEVICE

FIELD OF THE INVENTION

The present invention relates generally to a removable device for maintaining the shape of a wire, and more particularly to a removable angled guide wire storage device for maintaining the angle or shape of an end of a guidewire during transport and storage for subsequent use with a medical device such as an endoscope.

BACKGROUND OF THE INVENTION

An endoscope is a medical device that is used to examine a body cavity or interior surfaces of an organ or tissue. The endoscope includes a long, thin tube with a light and a video camera that may be inserted into a body, such as through a natural opening like a mouth or rectum, and directed through the body to the anatomy of interest for a medical professional. The endoscope may have one or more channels adapted for receiving a guidewire to assist in navigating the endoscope through cavities and passages in the body to examine a desired area.

A guidewire associated with an endoscope may have an angled distal end to assist in guiding the endoscope through channels of the body and reduce or prevent damage to inner walls surrounding the cavities or narrow channels as the endoscope passes through. During transport and storage prior to use of the guidewire in a medical procedure, an angled tip guidewire may have the tendency to straighten out due to the elastic recovery or loss of shape memory of the wire. For example, a 30° angle on an angled guidewire may relax to a 12° angle over the course of a shelf life of 1-5 years. Guidewires may be designed to navigate through the body at particular angles, and if these angles are not maintained prior to use, this may cause discomfort for the patient or difficulty for a medical professional to guide the endoscope through narrow channels in the body, for example.

Thus, what is needed is a device for maintaining the set angle or shape of the distal, end of the guidewire, such as during transport and storage, preventing the tip of the guidewire from puncturing or otherwise damaging additional packaging surrounding the guidewire and device, maintaining sterilization of the guidewire until the device is removed prior to use of the guidewire, protecting a distal tip of a guidewire, or any combination thereof.

SUMMARY OF THE INVENTION

The present teachings relate to an article comprising: i) a guidewire having a distal end and terminating at a distal tip, and ii) a removable angled guidewire storage device located about the distal end, wherein the removable angled guidewire storage device is generally tubular in shape and contains one or more internal structures for maintaining the angle of the distal end of the guidewire; and the distal end is maintained at an angle even after the removable angled guidewire storage device is removed due to the prolonged positional influence of the device during sterilization, transportation and storage. The present teachings also relate to a method of using the removable angled guidewire storage device. The method may include disposing a distal end of a guidewire in a removable angled guidewire storage device, wherein the removable angled guidewire storage device includes one more internal structures for maintaining the angle of the distal end of the guidewire; and packaging, storing, or both, the guidewire disposed in the removable angled guidewire storage device.

The present teachings may comprise a removable angled guidewire storage device including one or more internal structures for contacting the distal end of the guidewire. Such internal structures may include, but are not limited to, a spine, a channel, an inner wall, an inwardly projecting conical shape, or any combination thereof. The removable angled guidewire storage device may have one or more openings for receiving at least a portion of the distal end of the guidewire. The removable angled guidewire storage device may have a slit for receiving at least a portion of the distal end of the guidewire. The guidewire may be held within the removable angled guidewire storage device by friction fit. The removable angled guidewire storage device may have one or more open spaces. The removable angled guidewire storage device may have a generally solid outer surface.

The removable angled guidewire storage device may receive any type of guidewire. For example, the guidewire may have an internal wire with one or more outer casings. The guidewire may have a distal end forming an angle of about 45 degrees±about 15 degrees in relation to the remaining body portion of the guidewire. The distal end of the guidewire may be substantially J-shaped. The distal end of the guidewire may have an abrupt sharp corner or may have a smooth transition at the curved region. The distal end of the guidewire may have an alternative shape such as a corkscrew or spiral shape.

The article including an angled guidewire storage device as disclosed herein may allow for many benefits, including but not limited to: protecting an end of the guidewire, maintaining the angle of the end of the guidewire, reducing the likelihood of the guidewire puncturing or damaging packaging surrounding the guidewire, maintaining the sterilization of the guidewire within the sterile packaging, or any combination thereof.

DETAILED DESCRIPTION

The explanations and illustrations presented herein are intended to acquaint others skilled in the art with the invention, its principles, and its practical application. The specific embodiments of the present teachings as set forth are not intended as being exhaustive or limiting of the invention. The scope of the teachings should be determined not with reference to the description herein, but should be determined with reference to the appended claims, along with the full scope of equivalents to which such claims are entitled. The disclosures of all articles and references, including patent applications and publications, are incorporated by reference. Other combinations are also possible as will be gleaned from the following claims, which are also hereby incorporated by reference into this written description. One or more as used herein means that at least one, or more than one, of the recited components may be used as disclosed. The present teachings claim the benefit of the priority of the filing date of U.S. Provisional Application Ser. No. 62/007,958, filed Jun. 5, 2014, which is herein incorporated by reference for all purposes.

The teachings relate to an article comprising a guidewire and an angled guidewire storage device. A guidewire is a thin wire that can be inserted into a confined space or tortuous path to act as a guide for subsequent insertion of an instrument. A guidewire may include a long, thin body that includes a proximal end that terminates at a proximal tip and a distal end that terminates at a distal tip. One or more of the ends of the guidewire may include one or more angles or shaped portions. A shaped portion may include one or more portions shaped to facilitate insertion of the guidewire into a patient's body, for example a curved portion, a substantially J-shaped portion, a corkscrew portion or a spiral portion. An angled guidewire storage device may be located about an end of the guidewire to maintain an angle of the end of the guidewire or maintain a certain nonlinear shape, such as a curve or J-shape, for example, during transportation, storage, or both. The angled guidewire device is preferably a removable angled guidewire storage device, which means the device may be detached or otherwise removed from the guidewire prior to using the guidewire for its intended purpose. The removable angled guidewire storage device may also be generally tubular in shape. Tubular in shape means that the removable angled guidewire storage device includes one or more generally rounded portions and one or more generally hollow or open portions and may have a profile that proceeds in a generally longitudinal direction.

The teachings also relate to a method of using an angled guidewire storage device. The method may include disposing an end of a guidewire in a removable angled guidewire storage device, wherein the removable angled guidewire storage device includes one more internal structures for maintaining an angle of the end of the guidewire; and packaging, storing, or both, the guidewire disposed in the removable angled guidewire storage device. The one or more internal structures of the angled guidewire storage device may be any structure that functions to hold the wire at the desired angle, such as by contacting the wire at one or more points, and/or to prevent the wire from straightening or otherwise deviating from the desired angle. Examples of internal structures include, but are not limited to, a channel, an inner wall, a spine, an inwardly projecting conical shape, a corkscrew walled section, a spiral walled section, the like, or combination thereof.

The present teachings can be employed in any application requiring maintaining an angle or shape of a distal end of a wire, especially during transportation of the wire, storage of a wire, or both. It may be desirable to maintain an angled or shaped distal end of a wire in applications where the wire is directed to travel through channels. An angled distal end may ease the navigation of the wire through channels, especially channels having turns or bends. An exemplary application where it is desirable to maintain an angled or shaped distal end of a wire includes navigating a guidewire through a body, such as for use with a medical device. A medical device may be any device that functions to allow a medical professional to navigate through channels or spaces within a body. Examples of a medical device include an endoscope, cystoscope, or catheter.

In a preferred embodiment, the angled guidewire storage device is packaged with a guidewire, and optionally an introducer. An introducer is a device that functions to guide the distal end of the guidewire into a channel of a medical device so the guidewire can be used with the medical device. The angled guidewire storage device, though not limiting, may be used to protect the distal end of the guidewire, maintain the angle or shape of the distal end of the guidewire, reduce the likelihood of the guidewire puncturing or damaging the packaging, keep the guidewire sterile within the sterile packaging, or any combination thereof. The angled guidewire storage device is preferably removable, thereby allowing a user to detach the removable angled guidewire storage device prior to inserting the guidewire into a channel of a medical device, a channel of a body, or both.

A distal end of a guidewire exhibiting an angle or shape in relation to the body portion of the guidewire, and the method of maintaining this angle or shape, involves providing one or more structures for holding the guidewire at the desired angle or shape. Examples of shapes include any nonlinear shape, such as a curve or, for example, a substantially J shaped curve. The one or more structures may include any structure that functions to hold the end of the wire in the desired shape or at the desired angle; resist the tendency of the wire to relax, straighten, or otherwise deviate from the desired shape; or any combination thereof. Such structures may comprise any of the following elements individually or in any combination: one or more internal structures for maintaining the angle of the distal end of the guidewire including an inwardly projecting conical shape; one or more internal structures for maintaining the angle of the distal end of the guidewire including a spine that maintains the angle of the distal end of the guidewire; one or more internal structures for maintaining the angle of the distal ends of the guidewire including one or more inner walls; the removable angled guidewire storage device having a generally solid outer surface; the removable angled guidewire storage device having one or more openings for receiving at least the distal end of the guidewire; the removable angled guidewire storage device having a slit for receiving at least the distal end of the guidewire; or the guidewire being held within the removable angled guidewire storage device by friction fit.

The article as described herein may comprise a guidewire. Guidewires are used in medical procedures to provide additional structure and guidance to an associated medical device, especially a medical device for viewing channels, tissues, cavities, or spaces within a body. A guidewire may comprise a long, thin body portion that includes a proximal end that terminates at a proximal tip and a distal end that terminates at a distal tip. Generally, at least the distal tip and at least a portion of the distal end are inserted into the medical device, and subsequently the body, when used. Prior to use, the guidewire may be packaged in sterile packaging and remain untouched until the packaging is opened by a medical professional during the procedure employing the medical device. After use, the guidewire may be disposed.

The present teachings may use any type of guidewire that can be inserted into and navigated through a body. The guidewire may comprise any structure useful in guiding or directing medical devices through the body of a patient. The components of the guidewire may comprise any material suitable for use within a body. The guidewire may be constructed of a single material. The guidewire may comprise a core and one or more layers or casings. A core may include one or more structures that may provide strength and support for the guidewire and may assist a medical professional in navigating the guidewire through the body of a patient. A casing may be one or more layers at least partially covering the core that may function to provide flexibility to the guidewire, protect the core, reduce friction between the guidewire and the channels within the body of the patient, or combination thereof, for example. The core material and the casing materials may be different. The core of the guidewire may comprise one or more inner wires. The one or more inner wires may have a diameter that gradually tapers to a smaller diameter until the one or more inner wires terminate within the guidewire. The selected materials comprising the core may be beneficial to provide strength and stiffness to the guidewire so the guidewire can navigate through passages within a body. The materials may also exhibit sufficient shape memory to hold the shape into which it is formed (e.g., to hold the angle or curve at the distal end of the wire). Shape memory means that the material "remembers" and returns to its original shape when a particular event occurs, such as when it is heated to a certain temperature. For example, a shape memory alloy can be bent or stretched and will hold the deformed shape until heated above a transition temperature. The guidewire may exhibit superelasticity. Superelasticity is an elastic response to an applied stress. A material exhibiting superelasticity may return to its previous shape after the removal of even high applied strains. The core, such as one or more inner wires, may comprise a plastic, metal, metal alloy, glass, blends of materials, the like, or combination thereof. Common metals and metal alloys may include, but are not limited to nickel, titanium, stainless steel, cobalt alloys, such as MP35N or Duratherm 600, superelastic alloys such as nitinol, the like, or a combination thereof. An exemplary alloy may include a metal alloy of nickel and titanium such as nitinol wire. It is contemplated that mechanical or thermal processes may be carried out to manipulate the material properties of the material or combination of materials of choice, such as for example strain hardening or necking, strain extrusion, annealing, heating, quenching, freezing, dipping in oil, ease hardening or any combination thereof. Generally, a guidewire may have a cross-section sized to be suitable for insertion into and navigation through the body of a patient, for example a cross-section size of about 0.1 mm or greater, about 0.25 mm or greater, or more commonly about 0.5 mm or greater at its widest portion. A guidewire may have a cross-section of about 5 mm or less, about 2 mm or less, or even about 1 mm or less at its widest portion.

The guidewire may include one or more outer layers or casings over the core or inner wire. The outer easing may be smooth to reduce friction between the guidewire and the channels of the body. The outer easing may help hold the guidewire in place once it reaches the desired anatomy. The outer casing, especially at the distal tip of the guidewire, may allow for a more atraumatic entry into the body and the cavities. The materials employed for the outer casing may be chosen, based on the desired properties at temperatures encountered during use. For example, an outer casing may be formed from a material that minimally softens at the internal body temperature of the patient. The material may maintain a particular stiffness modulus to allow the guidewire to navigate through the body. In a preferred embodiment, the outer casing includes a polymer with an elastomeric nature. Elastomeric nature means that the material is able to resume its original shape once a deforming force is removed. It may be beneficial, to have a guidewire with an elastomeric nature to prevent injury or discomfort to the patient as the guidewire contacts inner walls of channels or cavities within the body. The outer casing may have a stiffness modulus of about 0.1 GPa or greater, more preferably about 0.2 GPa or greater, or even more preferably about 0.4 GPa or greater. The outer casing may have a stillness modulus that is about 1 GPa or less, more preferably about 0.6 GPa or less, or even more preferably about 0.5 GPa or less. The outer casing may have sufficient rigidity for holding its shape under normal usage conditions. This rigidity is beneficial for generally maintaining the desired angle upon insertion into channels in the body and assisting in navigating the guidewire and associated medical device through the body. The outer layers or casings may comprise materials that perform the recited functions, such as, but not limited to, polymers, metals, or metal alloys. Examples of useful polymers include polyurethane, thermoplastic elastomers, polytetrafluoroethylene, polybutylene, nylon, polyether block amide, the like, or combination thereof. Metals or alloys thereof in order to be in the appropriate stiffness range for this purpose, may need to be wound as a coil to form a casing and may include stainless steel including, but not limited to, alloys 302, 304, and 316, aluminum including, but not limited to, 6061 and 7075, titanium, titanium alloys, nickel, nickel alloys including, but not limited to, nitinol or elgiloy, cobalt alloys including, but not limited to, Duratherm 600 or MP35N, tungsten, the like, or combination thereof. It is contemplated that mechanical or thermal processes may be earned out to manipulate the material properties of the material or combination of materials of choice, such as for example strain hardening or necking, strain extrusion, annealing, heating, quenching, freezing, dipping in oil, ease hardening or any combination thereof.

The core or inner wire may terminate before the distal tip of the guidewire. Therefore, the one or more outer layers or casings may extend beyond where the inner wire terminates. The termination of the inner wire a particular distance from the distal tip of the guidewire may allow for increased flexibility in the distal tip of the guidewire, especially as the easing material may be a more flexible material than that of the inner wire. This additional flexibility may function to flex when traveling through the walls of the channels as the guidewire navigates through the body. For example, upon the distal tip contacting a wall, the absence of the inner wire at the immediate tip may allow the casing to flex or bend. The core, such as one or more inner wires, may terminate about 0.25 mm or greater, more preferably about 0.5 mm or greater, or even more preferably about 1 mm or greater from the distal tip of the guidewire. The core, such as one or more inner wires, may terminate about 5 mm or less, more preferably about 4 mm or less, or even, more preferably about 3 mm or less from the distal tip of the guidewire.

The distal end of the guidewire may include one or more shaped or angled portions. The shaped or angled portions function, to guide the distal tip of the guidewire through the body and assist with insertion and navigation into channels, cavities, and other areas of a body. The distal end of the guidewire may have an angle of about 30 degrees or greater, or more preferably about 40 degrees or greater in relation to the body portion, or the remaining portion, of the guidewire. The distal end of the guidewire may have an angle of about 60 degrees or less, or more preferably about 50 degrees or less in relation to the body portion, or the remaining portion, of the guidewire. For example, the distal end of the guidewire may have an angle of about 45 degrees in relation to the remaining portion, of the guidewire. Other shaped structures include nonlinear shapes. For example, the distal end of the guidewire may be substantially J-shaped, may have a corner that forms a sharp point, may have a smooth angle transition, may have a corkscrew or spiral configuration, or be otherwise curved.

An angled guidewire storage device functions to retain the angle or shape of the guidewire prior to use, such as during periods of shipping and storage. The guidewire may be packaged with the angled guidewire storage device. Packaging of the guidewire may be beneficial to keep the guidewire sterile until it is used. The angled guidewire storage device is preferably located about the distal end of the guidewire and may function to, for example, prevent the guidewire from puncturing the packaging, thereby compromising the sterile guidewire, maintain the angle or shape of the guidewire, protect the tip of the guidewire, or combination thereof. Preferably, the angled guidewire storage device is a removable angled guidewire storage device, meaning that the angled guidewire storage device is a distinct structure which may be physically separated from the guidewire. For example, the angled, guidewire storage device may maintain the angle or shape of the distal end of the guidewire during transport and storage and may be removed prior to using the guidewire.

The angled guidewire storage device may be constructed of a material with sufficient strength to resist the guidewire's tendency to straighten or otherwise deviate from the desired angle or curve. The angled guidewire storage device may be formed by any known process for shaping the chosen material into the desired shape, for example by injection molding or other shaping processes. The angled guidewire storage device may be formed from a polymer, metal, or metal alloy. Examples of useful polymers include polyurethane, thermoplastic elastomer, polytetrafluoroethylene, polybutylene, nylon, polyether block amide, polyethylene, polyethylene terephthalate, the like, or combination thereof. Example of useful, metals or alloys thereof include, stainless steel, including, but not limited to, alloys 302, 304, 316, aluminum including, but not limited to, 6061 7075, titanium, titanium alloys, nickel alloys including, but not limited to, nitinol or elgiloy, cobalt alloys including, but not limited to, Duratherm 600 or MP35N, tungsten, the like, or any combination thereof. It is contemplated that mechanical or thermal processes may be carried out to manipulate the material properties of the material, or combination of materials of choice, such as, for example, strain hardening or necking, strain extrusion, annealing, heating, quenching, freezing, dipping in oil, case hardening or any combination thereof.

The angled guidewire storage device may have any shape or structure that facilitates holding the guidewire at the desired angle or shape and protects the guidewire. The angled guidewire storage device may be generally tubular in shape. The profile of the angled guidewire storage device may be generally straight, and/or extend in a longitudinal direction. The profile of the angled guidewire storage device may be generally angled or curved in a longitudinal direction. For example, the angle or shape of the profile of the angled guidewire storage device may generally match the desired angle or shape of the distal end of the guidewire. The angled guidewire storage device may have a generally solid outer surface and may have one or more hollow areas for receiving and holding at least a portion of the distal end of the guidewire. The angled guidewire storage device may instead have a generally open structure having one or more supports or standoffs. The angled guidewire storage device may have one or more generally ring-like structures for receiving and encircling at least a portion of the distal end of the guidewire. The ring-like structures may be joined to each other by one or more supports such as standoffs or a spine. The ring-like structures may be connected by one or more standoffs or a spine to provide structure, maintain the distance between the ring-like structures, support the guidewire, or combination thereof. For example, one generally ring-like structure may receive and encircle a portion of the guidewire at or about a point proximal to the distal tip of the guidewire, and another generally ring-like structure may encircle a portion of the guidewire at or about the distal tip.

The angled guidewire storage device may contain one or more internal structures for maintaining the angle of the distal end of the guidewire. The one or more internal structures may include any structure that maintains the desired angle or shape of the distal end of the guidewire. The internal structures may be any structure that resists the guidewire's tendency to relax, straighten, or otherwise deviate from the desired angle or shape of the distal end of the guidewire. The internal structures described herein may be used alone or in any combination with each other to achieve and maintain the desired angle or shape of the distal end of the guidewire.

An angled guidewire storage device may have an internal channel, for receiving the guidewire. The channel may be formed by one or more inner walls, which may contact the guidewire and/or hold the guidewire in the particular angle. The one or more inner walls may be generally straight and proceed in a generally longitudinal direction. The one or more inner walls may generally form an angle, such as one that matches the desired shape or angle of the distal end of the guidewire. The angled guidewire storage device may have a spine associated with the device that may contact the guidewire and hold, the guidewire in the particular angle. For example, the spine may be located generally centrally within the angled guidewire storage device. The spine may connect two or more generally ring-like structures. The spine may be generally straight and proceed in a generally longitudinal direction. The spine may be generally angled, such as to match the desired angle or shape of the distal end of the guidewire. The angled guidewire storage device may include an inwardly projecting conical shape located at the distal end of the angled guidewire storage device. Inwardly projecting means that the vertex of the conical shape, or the portion with the smallest diameter, is directed toward the proximal end of the angled guidewire storage device. The angled portion of the distal end of the guidewire may be guided and held in the desired angle by the walls of the inwardly projecting conical shape. The inwardly projecting conical shape may also be used with another internal structure for maintaining the angle of the distal wire. For example, the angled guidewire storage device may include a spine for guiding part of the guidewire in a generally longitudinal direction, and upon contacting the inwardly projecting conical shape, the guidewire may be forced in another direction to hold the desired angle in relation to the portion of the guidewire in the generally longitudinal direction.

Preferably, when the guidewire is being used, at least the distal end is inserted into a working channel of a medical device. Such medical devices may generally be any medical device which is utilized for inserting a thin, elongated structure into a patient's body, such as, but not limited to, an endoscope, cystoscope, or catheter. An introducer may function to facilitate entry of the guidewire into the working channel of the medical device. An introducer is a device that stabilizes and guides a guidewire into the channel of the medical device. The introducer may also limit movement of the guidewire. The introducer may surround a portion of the guidewire adjacent to the distal end of the guidewire. The introducer may include a hollow channel into which the guidewire is inserted. When used, the introducer may force the angled distal end of the guidewire or the generally J-shaped distal end of the guidewire to straighten to allow the guidewire to be inserted into the working channel of the medical device. The introducer may have any shape or structure that can be utilized for inserting a thin, elongated structure into a medical device, which may include, but is not limited to, a needle-like portion; a long, gradually tapered tip; a butterfly-shaped portion; a trigger; a handle; the like; or any combination thereof. The introducer may be provided in a package with the guidewire and removable angled guidewire storage device. The packaging may be a sterile package that is opened by a medical professional during a procedure employing the contents of the package. The removable angled guidewire storage device may be connected to at least a portion of the introducer, for example, during transportation and storage.

The angled guidewire storage device may be located about the distal end of the guidewire by inserting the distal tip and sliding the distal end through one or more openings in the angled guidewire storage device or by sliding the one or more openings over the wire. Alternatively, the angled guidewire storage device may include a slit for receiving at least the distal end of the guidewire. Upon disposing the guidewire in the angled guidewire storage device, the guidewire may be held within the angled guidewire storage device by arty structure that is adapted to hold the guidewire in a desired position, including, but not limited to, friction fit, a series of ring-like structures, channels, inner walls, corkscrew or spiral shaped channels, or a combination thereof. The one or more openings may fit over, secure to, or otherwise connect to an introducer if an introducer is included within the packaging of the guidewire. The one or more generally ring-like structures may include a slit for snapping over the guidewire or an introducer. The introducer or guidewire may be held within the one or more generally ring-like structures by friction fit. To remove the angled guidewire storage device, the device may slide out through the same opening in which it entered. The angled guidewire storage device may be removed by forcing the guidewire from the slit of the angled guidewire storage device and/or the slit from the generally ring-like structure. The angled guidewire storage device may unsnap from the introducer or the wire. The angled guidewire storage device may alternatively be broken or cut away from the guidewire.

The teachings herein include the method of using the angled guidewire storage device, especially for maintaining the desired angle or shape of the distal end of the guidewire. The method may comprise disposing at least a portion of the distal end of the guidewire in the angled guidewire storage device. The angled guidewire storage device includes one or more internal structures, which maintain the angle or shape of the distal end of the guidewire. The method may include packaging, storing, or both, the guidewire disposed in the angled guidewire storage device. The method may also include shipping the guidewire and angled guidewire storage device to a desired recipient, including but not limited to, a distributor, hospital, medical professional's office, medical supply store or vendor, end user, or combination thereof.

The disposing step may involve any action that results in at least a portion of the guidewire being generally supported by the angled guidewire storage device. The angled guidewire storage device may have one or more openings for receiving at least the distal end of the guidewire. The one or more openings may be any type of opening capable of receiving at least a portion of the guidewire, which may include, but are not limited to, one or more ring-like structures, one or more slits, one or more holes, the like, or any combination thereof. The disposing step of the method may include inserting the distal tip and at least a portion of the distal end of the guidewire into the one or more openings. The disposing step may include sliding the opening, such as one or more ring-like structures, over the distal tip and/or at least a portion of the distal end of the guidewire. The disposing step may instead include inserting the distal end of the guidewire into the slit. The distal end of the guidewire may then be held within the angled guidewire storage device by any structure that is adapted to hold the guidewire in a desired position, including, but not limited to, friction fit, a series of ring-like structures, channels, inner walls, corkscrew or spiral shaped channels, or a combination thereof.

When a medical professional is using the guidewire disposed in the angled guidewire storage device, the medical professional may remove any packaging surrounding the guidewire and the angled guidewire storage device. The medical professional may remove the angled guidewire storage device by any method that physically separates the angled guidewire storage device from the distal end of the guidewire. For example, the angled guidewire storage device may be removed by pulling the guidewire through the same one or more openings that it traveled through during the disposing step. After the angled guidewire storage device is removed, it may be discarded, recycled, or sterilized and/or repackaged. The medical professional may then introduce the distal end of the guidewire, and optionally temporarily straighten the angled or shaped portion of the guidewire, such as by using an introducer, into the medical device and subsequently the body of the patient. After the guidewire has been used, it may be discarded, recycled, or sterilized and repackaged.

Figure 1:
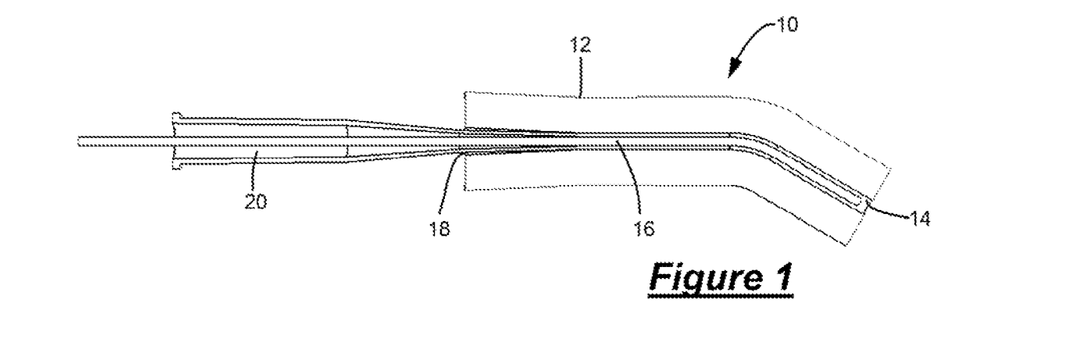
FIG. 1 exemplifies a removable angled guidewire storage device having a solid outer surface and a channel for receiving and maintaining a guidewire.

FIG. 1 shows an exemplary removable angled guidewire storage device 10. The removable angled guidewire storage device 10 includes a solid outer surface 12 and a channel 14 within the removable angled guidewire storage device 10 for receiving the guidewire 16. The exemplary removable angled guidewire storage device 10 includes an angled profile generally matching the desired angle of the distal end of the guidewire 16 and allows the removable angled guidewire device 10 to maintain the desired angle of the distal end of the guidewire 16. The proximal opening 18 of the removable angled guidewire storage device 10 fits over at least a portion of the introducer 20.

Figure 2:
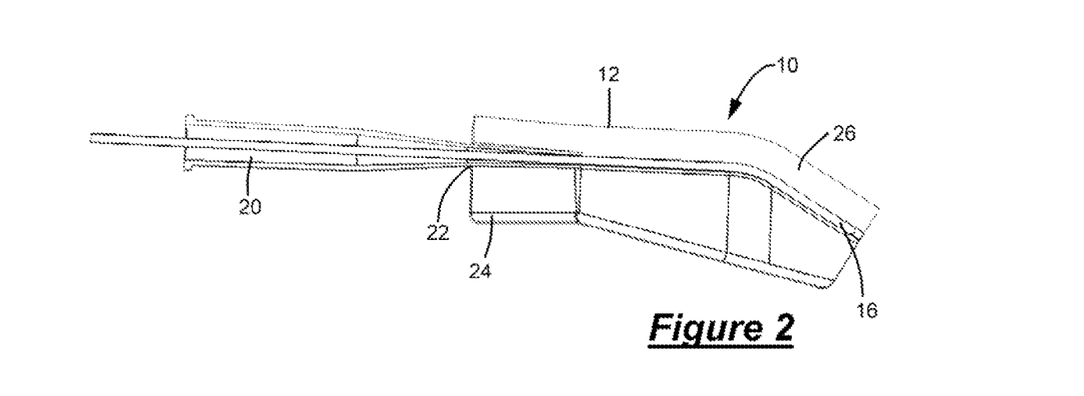
FIG. 2 exemplifies a removable angled guidewire storage device having a solid outer surface and a slit for receiving a guidewire.

FIG. 2 shows another exemplary angled guidewire storage device 10. The removable angled guidewire storage device 10 includes a solid outer surface 12. The removable angled guidewire storage device 10 includes a slit 22 for inserting the guidewire 16 into the removable angled guidewire storage device 10, and the guidewire 16 is held within the removable angled guidewire storage device 10 by friction fit. The removable angled guidewire storage device 10 includes an angled portion 26 which contacts and holds the guidewire 16 and generally matches the desired angle of the distal end of the guidewire 16. Exhibited is a generally triangular profile for the removable angled guidewire storage device 10, where there is a generally straight portion 24 to accommodate the slit 22 and the generally angled portion 26 to maintain the angle of the distal end of the guidewire 16. Other embodiments, including a generally straight profile or a generally angled profile including an angled portion accommodating the slit are also within the scope of the teachings herein.

Figure 3:
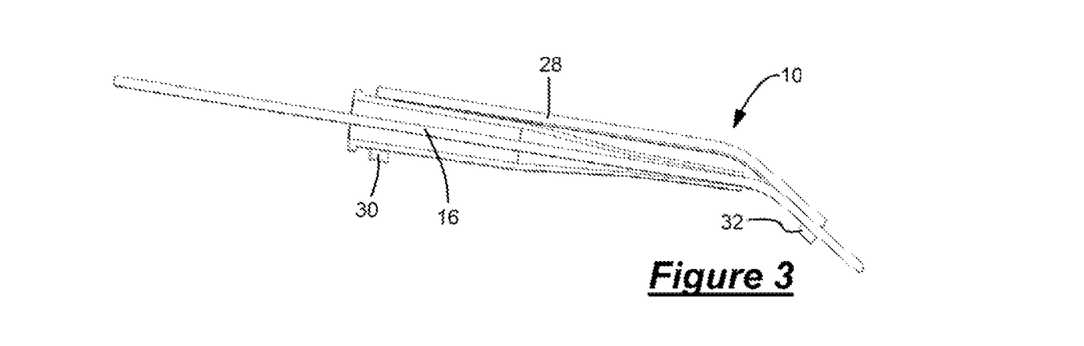
FIG. 3 exemplifies a removable angled guidewire storage device having two generally ring-like structures and a spine.

FIG. 3 shows another exemplary angled guidewire storage device 10. This removable angled guidewire storage device 10 includes one or more generally ring-like structures connected by a spine 28. In this embodiment, the spine 28 is angled to generally match and maintain the desired angle of the distal end of the guidewire 16. A first generally ring-like structure 30 may receive a portion of the guidewire 16 or an introducer 20 (see FIG. 1). The second, generally ring-like structure 32 may receive the distal tip of the guidewire 16.

Figure 4:
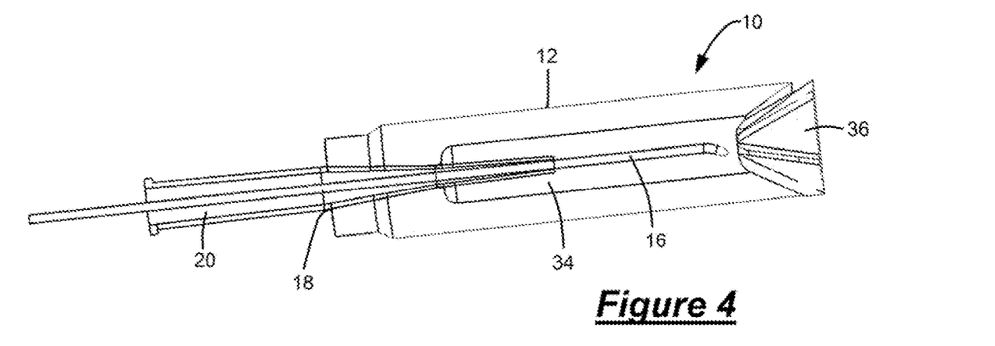
FIG. 4 exemplifies a removable angled guidewire storage device having a solid outer surface and an inwardly projecting conical shape.

FIG. 4 shows another exemplary angled guidewire storage device 10. This removable angled guidewire storage device 10 includes a solid outer surface 12 with a hollow portion 34 for receiving the distal end of the guidewire 16. The distal end of the angled guidewire storage device 10 includes a conical shape 36 that projects inwardly into the hollow portion 34 of the removable angled guidewire storage device 10. A narrow channel within the removable angled guidewire storage device 10 is also possible to provide further support to the guidewire 16 within the removable angled guidewire storage device 10. The walls of the inwardly projecting conical shape 36 guide and maintain the angled portion of the distal end of the guidewire 16. The distal end of the guidewire 16 may be disposed in an opening at the proximal end 18 of the removable angled guidewire storage device 10, and the angled portion is held in the desired angle by the walls of the inwardly projecting conical shape 36. The opening at the proximal end 18 of the removable angled guidewire storage device 10 may also receive and connect to at least a portion of an introducer 20.

Figure 5:
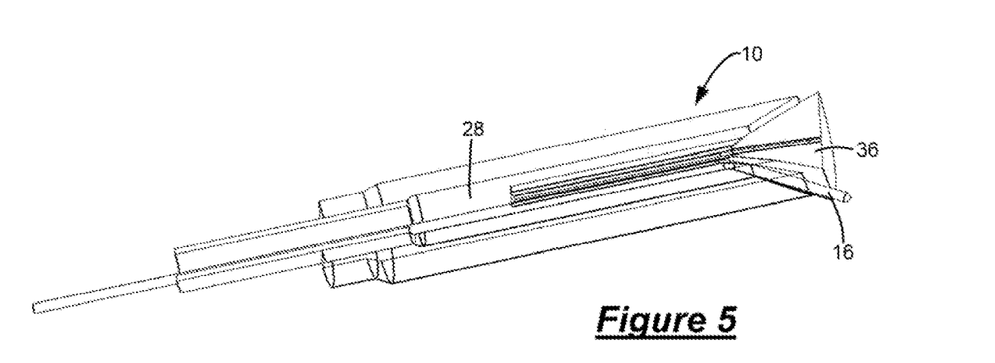
FIG. 5 exemplifies the removable angled guidewire storage device of FIG. 4 also including a generally centrally located spine.

FIG. 5 shows the exemplary angled guidewire storage device 10 of FIG. 4 with a spine 28 located generally centrally within the removable angled guidewire storage device 10. The spine 28 may provide further support to the generally longitudinally extending portion of the guidewire 16 before the angled portion of the distal end of the guidewire. The spine 28 may also provide additional resistance to the guidewire's tendency to relax, straighten, or otherwise deviate from the set angle.

Figure 6:
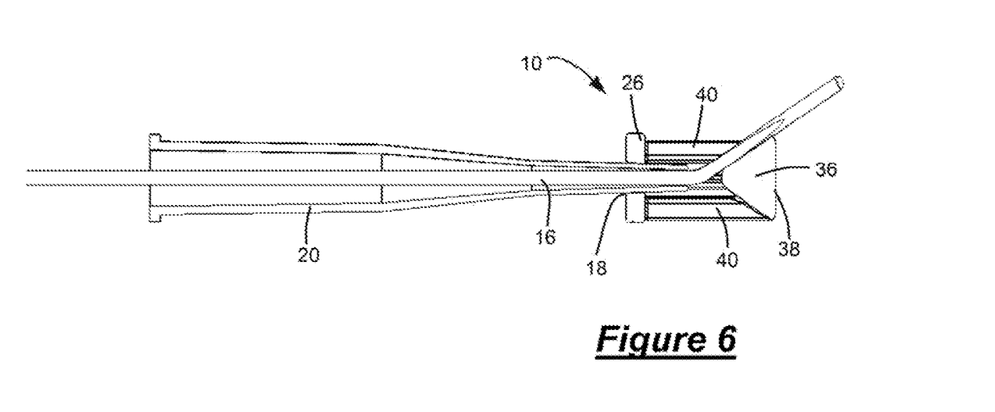
FIG. 6 exemplifies a removable angled guidewire storage device having a generally ring-like structure and an inwardly projecting conical shape.

FIG. 6 shows another exemplary angled guidewire storage device 10. This removable angled guidewire storage device 10 includes a generally ring-like structure 26 at the proximal end 18 of the removable angled guidewire storage device 10 for receiving the guidewire 16 and/or an introducer 20. The distal end 38 of the removable angled guidewire storage device 10 includes an inwardly projecting conical shape 36. The generally ring-like structure 26 and the inwardly projecting conical shape 36 are connected by one or more supports or standoffs 40. In this embodiment, the guidewire 16 can be disposed in the generally ring-like structure 26 and the angled portion of the guidewire 16 can be held in place by the walls of the inwardly projecting conical shape 36.

The article and method disclosed above are intended to serve as exemplary illustrations of the scope of the teachings. While the teachings herein discuss a removable angled guidewire storage device located about the distal end of a guidewire, this does not exclude a guidewire storage device on the proximal end of the guidewire. It is also within the scope of the teachings that the removable angled guidewire storage device may be used in applications outside of medical devices for maintaining angles of wires or other tools or structures.

Any numerical values recited in the above application include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32, etc. are expressly enumerated in this specification. For values which are less than one, one unit is considered to be 0.0001, 0.001, 0.01, or 0.1 as appropriate. These are only examples of what is specifically intended and all possible combinations of numerical values between the lowest value, and the highest value enumerated are to be expressly stated in this application in a similar manner. Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

What is claimed is:

1. An article comprising:
   i) a guidewire having an angled portion that is arranged at an angle relative to a remainder of the guidewire, and
   ii) a removable angled guidewire storage device,
   wherein a distal end of the removable angled guidewire storage device comprises a conical shape having a wall configured to contact and maintain the angled portion of the guidewire at the angle relative to the reminder of the guidewire;
   wherein a larger end of the conical shape is located distal of a smaller end of the conical shape;
   wherein a proximal end of the removable angled guidewire storage device comprises an opening that is adapted to fit over at least a portion of an introducer; and
   wherein the angled guidewire storage device includes an internal channel having walls extending between the conical shape and the opening at the proximal end of the angled guidewire storage device for receiving and holding the guidewire.

2. The article of claim 1, wherein the removable angled guidewire storage device is removed prior to using the guidewire.

3. The article of claim 1, wherein the angled portion is arranged at an angle of about 45 degrees in relation to a body portion of the guidewire.

4. The article of claim 1, wherein a distal end of the guidewire is substantially J-shaped.

5. The article of claim 1, wherein the guidewire comprises an inner wire and an outer casing.

6. The article of claim 5, wherein the inner wire of the guidewire exhibits sufficient shape memory and superelasticity and comprises a metal, metal alloy, nickel, titanium, or nitinol wire.

7. The article of claim 6, wherein the outer casing includes a polymer with an elastomeric nature having a stiffness modulus of 0.4 GPa or greater and sufficient rigidity for holding its shape under normal usage conditions.

8. The article of claim 5, wherein the inner wire of the guidewire tapers in diameter and terminates about 1 mm to about 3 mm from the distal tip of the guidewire.

9. The article of claim 1, wherein the angled portion is a distal end of the guidewire.

10. A method comprising:
   disposing an angled portion of a guidewire into a proximal end of a removable angled guidewire storage device, the angled portion is arranged at an angle relative to a reminder of the guidewire, the removable angled guidewire storage device includes a conical shape having a wall that is configured to contact and maintain the angle of the angled portion relative to the remainder of the guidewire, and an internal channel having walls for receiving and holding the guidewire, a larger end of the conical shape is located distal of a smaller end of the conical shape; and
   packaging, storing, or both the guidewire disposed in the removable angled guidewire storage device.

11. The method of claim 10, wherein the angled portion is a distal end of the guidewire.

12. The method of claim 10, wherein the conical shape is inwardly facing such that a vertex of the conical shape faces a proximal end of the removable angled guidewire storage device.

13. The method of claim 10, wherein the method comprises fitting an opening at the proximal end of the removeable angled guidewire storage device over an introducer.

14. An article comprising:
   i) a guidewire having an angled portion that is angled relative to a remainder of the guidewire; and
   ii) a storage device comprising a proximal end into which the guidewire is inserted, and an opposing distal end comprising a structure configured to contact the angled portion of the guidewire;
   wherein the structure comprises a conical shape that is inwardly facing such that a vertex of the conical shape is arranged closer to the proximal end of the storage device than the distal end of the storage device; and
   wherein the structure comprises a larger opening and an opposing smaller opening, the larger opening is located distal of the smaller opening.

15. The article of claim 14, wherein the angled portion is a distal end of the guidewire.

16. The article of claim 14, wherein the proximal end of the storage device comprises an opening that is adapted to fit over at least a portion of an introducer.

* * * * *